(12) United States Patent
Lee et al.

(10) Patent No.: US 9,842,722 B2
(45) Date of Patent: Dec. 12, 2017

(54) ELECTRON MICROSCOPE HAVING A CARRIER

(71) Applicant: Industrial Technology Research Institute, Hsinchu (TW)

(72) Inventors: Hsin-Hung Lee, Miaoli County (TW); Cheng-Yu Lee, Taipei (TW); Chun-Lin Chiang, New Taipei (TW); Kun-Chih Tsai, Hsinchu (TW); Win-Ti Lin, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 140 days.

(21) Appl. No.: 14/964,586

(22) Filed: Dec. 10, 2015

(65) Prior Publication Data
US 2016/0172152 A1 Jun. 16, 2016

(30) Foreign Application Priority Data
Dec. 10, 2014 (TW) .............................. 103143021 A (51) Int. Cl.
*H01J 37/18* (2006.01)
*H01J 37/20* (2006.01)
(Continued)

(52) U.S. Cl.
CPC .............. *H01J 37/20* (2013.01); *H01J 37/28* (2013.01); *G01N 35/1095* (2013.01);
(Continued)

(58) Field of Classification Search
CPC .. H01J 37/16; H01J 37/18; H01J 37/20; H01J 37/26; H01J 37/28; H01J 37/29;
(Continued)

(56) References Cited

U.S. PATENT DOCUMENTS

| 5,735,129 A | 4/1998 | Ienaga |
| 6,989,542 B2 | 1/2006 | Moses et al. |

(Continued)

FOREIGN PATENT DOCUMENTS

| CN | 86103602 | 12/1987 |
| CN | 1511332 | 7/2004 |

(Continued)

OTHER PUBLICATIONS

"Office Action of China Counterpart Application," dated Apr. 5, 2017, p. 1-p. 6.
(Continued)

*Primary Examiner* — Phillip A Johnston
*Assistant Examiner* — Hsien Tsai
(74) *Attorney, Agent, or Firm* — JCIPRNET (57) ABSTRACT

An electronic microscope includes a carrier, a first driving unit, a flow-buffer unit and an electron source. The carrier carries a sample. The first driving unit drives a first fluid to flow along a first flow path, wherein the first flow path passes through the sample. The flow-buffer unit is disposed on the first flow path to perform buffering on the first fluid, wherein the first fluid flows through the flow-buffer unit and the carrier in sequence. The electron source provides an electron beam to the sample.

22 Claims, 7 Drawing Sheets

(51) Int. Cl.
*H01J 37/28* (2006.01)
*G01N 35/10* (2006.01)

(52) U.S. Cl.
CPC ... *H01J 2237/18* (2013.01); *H01J 2237/2004* (2013.01); *H01J 2237/2065* (2013.01)

(58) Field of Classification Search
CPC .......... H01J 2237/006; H01J 2237/206; H01J 2237/2001; H01J 2237/2002; H01J 2237/2003; H01J 2237/2004; H01J 2237/2005; H01J 2237/2007; H01J 2237/2807; F25D 3/10
See application file for complete search history.

(56) References Cited

U.S. PATENT DOCUMENTS

| | | | |
|---|---|---|---|
| 6,992,300 | B2 | 1/2006 | Moses et al. |
| 2007/0045559 | A1 | 3/2007 | Chao et al. |
| 2008/0073532 | A1* | 3/2008 | Chao ............... H01J 37/18 250/310 |
| 2008/0179518 | A1 | 7/2008 | Creemer et al. |
| 2009/0166536 | A1 | 7/2009 | Suga et al. |
| 2012/0182548 | A1* | 7/2012 | Harb ............... G01N 21/05 356/246 |
| 2012/0298883 | A1 | 11/2012 | Grogan et al. |
| 2012/0305769 | A1* | 12/2012 | Yaguchi ............ H01J 37/20 250/310 |
| 2013/0155413 | A1 | 6/2013 | Liesener et al. |
| 2013/0264476 | A1 | 10/2013 | Damiano, Jr. et al. |

FOREIGN PATENT DOCUMENTS

| | | |
|---|---|---|
| CN | 101089617 | 12/2007 |
| CN | 101551513 | 10/2009 |
| CN | 102692495 | 9/2012 |
| CN | 103348439 | 10/2013 |
| CN | 103493171 | 1/2014 |
| JP | 2014026840 | 2/2014 |
| TW | I276139 | 3/2007 |
| TW | 200730789 | 8/2007 |
| TW | I296708 | 5/2008 |
| TW | I307521 | 3/2009 |
| TW | 201035533 | 10/2010 |
| TW | 201129775 | 9/2011 |
| TW | 201316371 | 4/2013 |
| TW | M475816 | 4/2014 |

OTHER PUBLICATIONS

"Office Action of Taiwan Counterpart Application", dated Jan. 21, 2016, p. 1-p. 7.

De Jonge et al., "Electron microscopy of specimens in liquid," Nature Nanotechnology, Nov. 2011, pp. 695-704.

Huang et al., "Self-aligned wet-cell for hydrated microbiology observation in TEM," Lab on a Chip, Nov. 30, 2011, pp. 340-347.

Mueller et al., "Nanofluidic Cells with Controlled Pathlength and Liquid Flow for Rapid, High-Resolution In Situ Imaging with Electrons," J. Phys. Chem. Lett., Jun. 26, 2013, pp. 2339-2347.

"Office Action of Japan Counterpart Application", dated Dec. 20, 2016, p. 1-p. 2.

* cited by examiner

FIG. 9

# ELECTRON MICROSCOPE HAVING A CARRIER

CROSS-REFERENCE TO RELATED APPLICATION

This application claims the priority benefit of Taiwan application serial no. 103143021, filed on Dec. 10, 2014. The entirety of the above-mentioned patent application is hereby incorporated by reference herein and made a part of this specification.

TECHNICAL FIELD

The disclosure relates to an electron microscope, and particularly relates to an electron microscope having a carrier.

BACKGROUND

Generally speaking, equipment such as atomic force microscopy (AFM) or electron microscope is commonly used to observe the geometric appearance of a substance at nano-level. When measuring using an AFM, a probe must be used to measure the geometric appearance of a sample. Such measurement process not only breaks the tip of the probe easily and takes a long time for measurement, but the measurement range of a sample is also narrower. The electron microscope, on the other hand, is free of such issues.

Taking scanning electron microscope (SEM) as an example, such microscope may be used to observe a liquid sample. When observing a liquid sample, a fluid needs to be driven to flow through a film carrying the sample to take away the metabolite of the sample, or the fluid needs to serve as a medium to add an agent required for the measurement to the sample. In such process, how to prevent the film from being damaged due to a disturbance of the fluid and how to control the temperature of the fluid flowing through the sample based on an observation requirement is a crucial factor in determining whether the liquid sample can be observed successfully. Also, the electron microscope may require an additional space and cost to implement a driving source for driving the flow of the liquid.

SUMMARY

An electron microscope according to an embodiment of the disclosure includes a carrier, a first driving unit, a flow-buffer unit, and an electron source. The carrier carries a sample. The first driving unit drives a first fluid to flow along a first flow path. In addition the first flow path passes through the sample. The flow-buffer unit is disposed on the first flow path to perform buffering on the first fluid. In addition, the first fluid flows through the flow-buffer unit and the carrier. The electron source provides an electron beam to the sample.

An electron microscope according to an embodiment of the disclosure includes a carrier and an electron source. The carrier includes a body and a film. The body has a first passage, and the first passage has a flow-buffer inclined surface. The film is disposed at the body and carries a sample. The sample is located in the first passage, and a first fluid flows along the first passage to pass through the flow-buffer inclined surface and the sample. The electron source provides an electron beam to the sample.

An electron microscope according to an embodiment of the disclosure includes a carrier and an electron source. The carrier includes a body and a film. The body has a first passage and a second passage. In addition, the first passage and the second passage are stacked with respect to each other. The film is disposed at the body and carries a sample. In addition, the sample is located in the first passage, a first fluid flows along the first passage and passes through the sample, and a second fluid flows along the second passage to adjust a temperature of the first fluid. The electron source provides an electron beam to the sample.

An electron microscope according to an embodiment of the disclosure includes a carrier, a flow-buffer unit, and an electron source. The carrier has a film carrying a sample. The flow-buffer unit has two channels. The first fluid flows through one of the channels and the sample, a second fluid flows through another one of the channels and the carrier to adjust a temperature of the first fluid, and the flow-buffer unit respectively performs buffering on the first fluid and the second fluid. The electron source provides an electron beam to the sample.

An electron microscope according to an embodiment of the disclosure includes a first chamber, a carrier, an evacuating module, and an electron source. The carrier is disposed inside the first chamber and carries a sample. The evacuation module evacuates the first chamber and drives a first fluid to flow through the sample. The electron source provides an electron beam to the sample.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

The disclosure provides an electron microscope capable of effectively performing buffering and temperature control on a sample and reducing a size and cost of the electron microscope.

Based on above, in the electron microscope according to the embodiments of the disclosure, buffering is performed on the first fluid by the flow-buffer unit and then the first fluid flows into the carrier. In addition, the flow-buffer inclined surface may also be used to perform buffering on the first fluid again, so as to further reduce a disturbance of the first fluid flowing through the sample in the carrier. Thus, the user is able to observe the sample by using the electron microscope successfully. Moreover, in addition to the first passage provided for the first fluid to flow through, the second passage stacked with respect to the first fluid may be also provided in the carrier for the second fluid to flow through, so that the temperature of the first fluid may be adjusted by using the second fluid. In this way, the sample may be observed at an expected suitable temperature. The already existing evacuation apparatus of the electron microscope may be further used to drive the first fluid to flow. In this way, it does not require an additional pump as the driving source of the first fluid, and the space and cost of the electron scope may thus be reduced.

Figure 1:
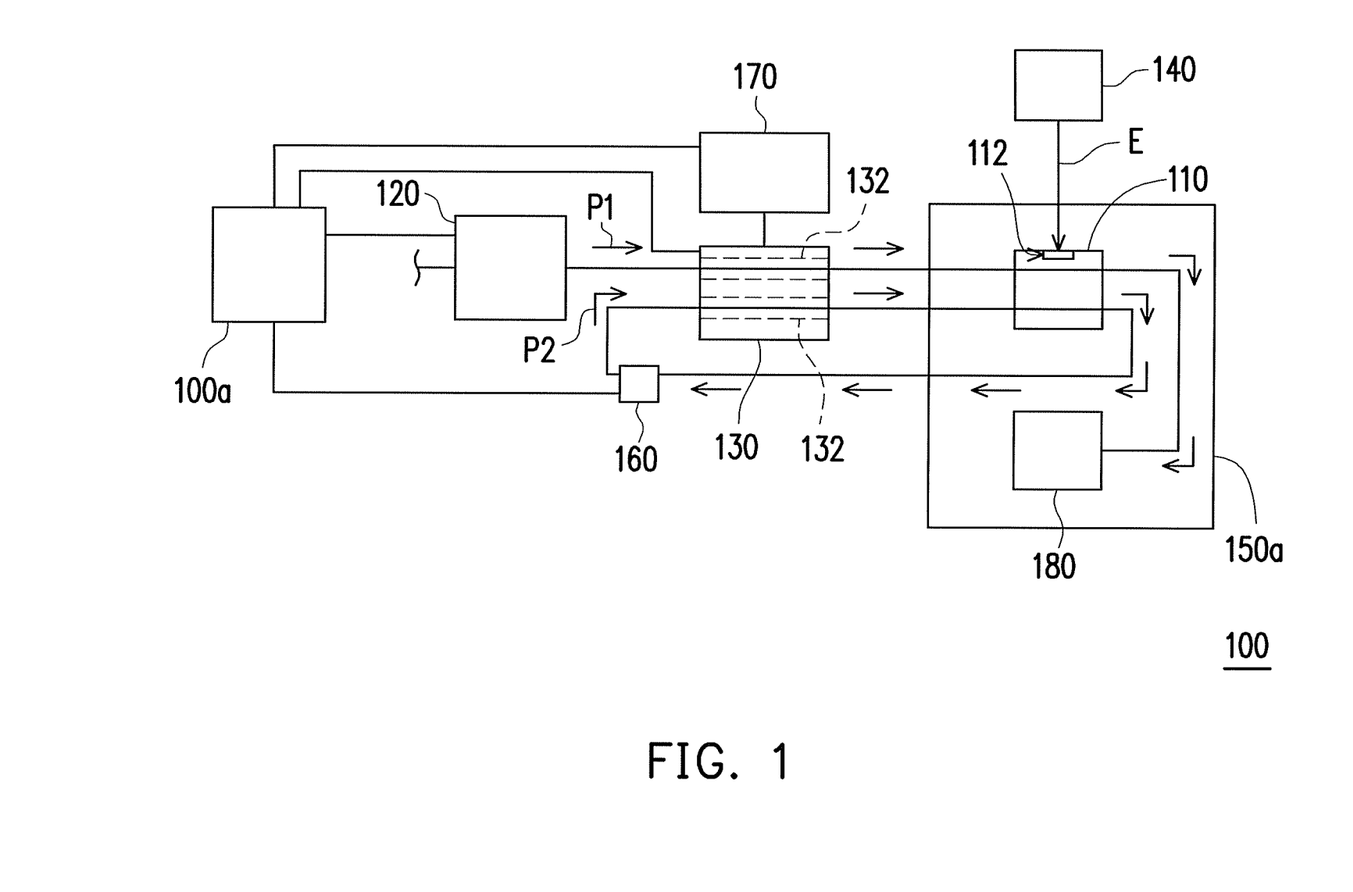
FIG. 1 is a schematic view illustrating some components of an electron microscope according to an embodiment of the disclosure.

FIG. 1 is a schematic view illustrating some components of an electron microscope according to an embodiment of the disclosure. Referring to FIG. 1, an electron microscope 100 of this embodiment is a scanning electron microscope, for example, and includes a carrier 110, a first driving unit 120, a flow-buffer unit 130, and an electron source 140. The carrier 110 is disposed in a first chamber 150a and has a film 112. The film 112 is configured to carry a sample (e.g., a liquid sample of biological cells), and the first chamber 150a is a vacuum chamber for observation of the sample. The electron source 140 is configured to provide an electro beam E to the sample for observation.

The first driving unit 120 is a pump, for example, and drives a first fluid to flow along a first flow path P1. In addition, the first fluid flows along the first flow path P1 and passes through the sample on the film 112, so as to carry away metabolite of the sample and collect the metabolite in a collection unit 180, or add an agent for measurement of the sample to the sample by using the first fluid as a medium. The first driving unit 120 is electrically connected to a control unit 100a of the electron microscope 100, for example, and operated under the control of the control unit 100a. The flow-buffer unit 130 is disposed on the first flow path P1 and located outside the first chamber 150a. The first fluid flows through the flow-buffer unit 130 and the carrier 110. The flow-buffer unit 130 is configured to perform buffering on the first fluid and reduce a disturbance of the first fluid. The flow-buffer unit 130 is also electrically connected to the control unit 100a, for example, and operated under the control of the control unit 100a. In an embodiment, a pipe connected to the flow-buffer unit 130 is configured to penetrate an outer wall of the first chamber 150a from outside of the first chamber 150a into inside of the first chamber 150a, such that the first fluid arrives at the carrier 110 inside the first chamber 150 via the pipe through driving of the first driving unit 120.

Figure 2:
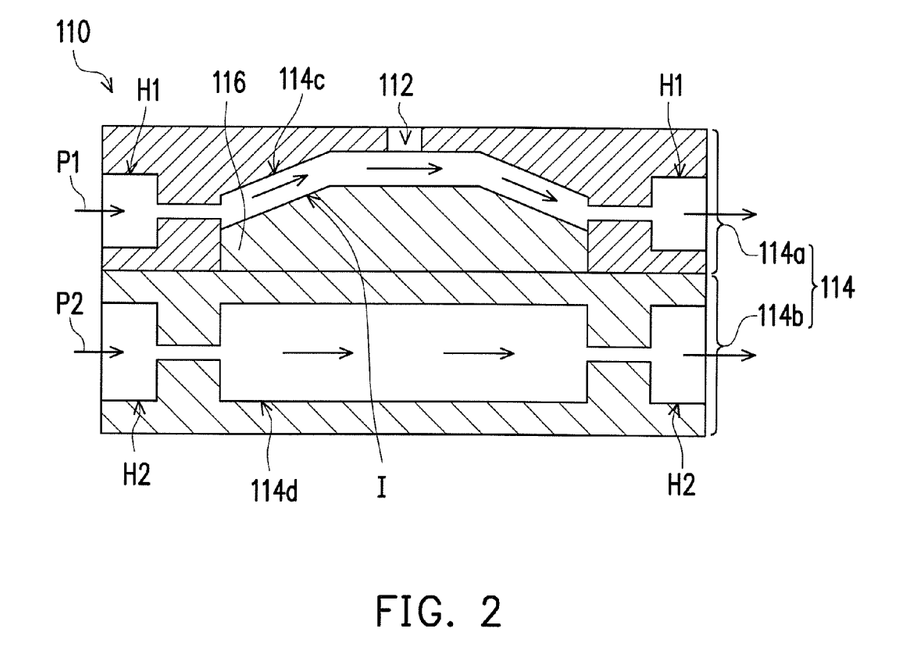
FIG. 2 is a partial structural cross-sectional view of a carrier shown in FIG. 1.

FIG. 2 is a partial structural cross-sectional view of a carrier shown in FIG. 1. Referring to FIG. 2, the carrier 110 includes a body 114. The body 114 includes an upper structure 114a and a lower structure 114b, for example. In addition, the upper structure 114a has a first passage 114c located on the first flow path P1, and the first passage 114c passes through the film 112 to allow the sample to be located in the first passage 114c. The carrier 110 further includes a protrusion structure 116. The protrusion structure 116 is located in the first passage 114c and form a flow-buffer inclined surface I in the first passage 114c. The first fluid flows along the first passage 114c to pass through the flow-buffer inclined surface I and the sample on the film 112. With such design, buffering is not only performed on the first fluid before arriving at the carrier 110 by using the flow-buffer unit 130 but also performed after the first fluid enters the carrier 110 by using the flow-buffer inclined surface I before flowing to the film 112, so as to prevent the film from being damaged due to an excessive disturbance of the first fluid.

Figure 3:
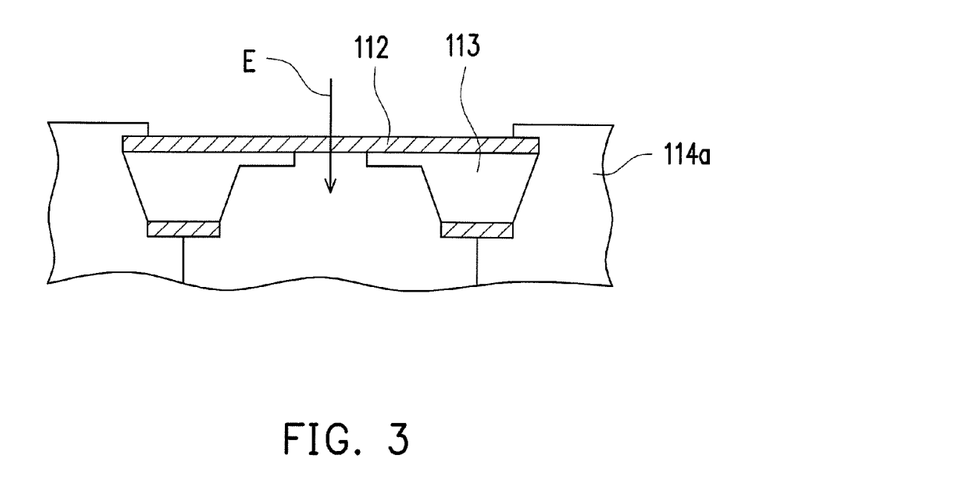
FIG. 3 is an enlarged view illustrating an embodiment of a portion of the carrier shown in FIG. 2 at a film.

FIG. 3 is an enlarged view illustrating an embodiment of a portion of the carrier shown in FIG. 2 at a film. The film 112 of this embodiment is a silicon nitride layer formed on a substrate 113 by performing a semiconductor manufacturing process, for example, and the substrate 113 is a silicon substrate, for example. The electron beam E may pass through the silicon nitride layer to function at the sample. In other embodiments, the film 112 may be formed of other suitable materials and manufactured by performing other suitable processes. The disclosure does not intend to impose any limitation in this regard.

In an embodiment, the electron microscope 100 may include a second driving unit 160 as shown in FIG. 1. The second driving unit 160 is configured to drive a second fluid to flow along a second flow path P2, and the second flow path P2 passes through the carrier 110. The second driving unit 160 is electrically connected to the control unit 100a, for example, and operated under the control of the control unit 100a. A pipe is disposed to penetrate the outer wall of the first chamber 150a from the outside of the first chamber 150a to the inside of the first chamber 150a, such that the second fluid arrives at the carrier 110 inside the first chamber 150a via the pipe through driving of the second driving unit 160. As shown in FIG. 2, the lower structure 114b of the body 114 of the carrier 110 has a second passage 114d on the second flow path P2, such that the second fluid flows along the second passage 114d. In addition, the first passage 114c and the second passage 114d are stacked with respect to each other. The second fluid may be controlled to have a suitable temperature and flow through the second passage 114d in circulation, so as to control a temperature of the sample in the adjacent first flow passage 114c. In other embodiments, a temperature regulation module may also be disposed in the carrier 110 to adjust the temperature of the sample in the first passage 114c, and the disclosure does not intend to impose a limitation in this regard.

Referring to FIG. 1, in an embodiment, the flow-buffer unit 130 may have two channels 132. The first flow path P1 and the second flow path P2 respectively pass through the channels 132. The flow-buffer unit 130 may respectively perform buffering on the first fluid and the second fluid. In addition, the flow-buffer unit 130 may perform buffering on the first fluid and the second fluid by respectively applying pressures to the channels 132. Also, the electron microscope 100 further includes a temperature control unit 170. The temperature control unit 170 may include a cooling chip and be connected to the flow-buffer unit 130, so as to control the temperatures of the first fluid and the second fluid flowing through the channels 132, thereby ensuring the first fluid and the second fluid flowing through the carrier 110 have expected temperatures. The temperature control unit 170 is electrically connected to the control unit 100a and operated under the control of the control unit 100a. In an embodiment, the first flow path P1 and the second flow path P2 are arranged in one flow-buffer unit 130. Thus, the flow-buffer unit 130 may perform buffering on the first fluid and the second fluid at the same time, and the temperature control unit 170 may simultaneously control the temperatures of the first fluid and the second fluid, so as to improve flow-buffer and temperature control efficiencies.

Figure 4:
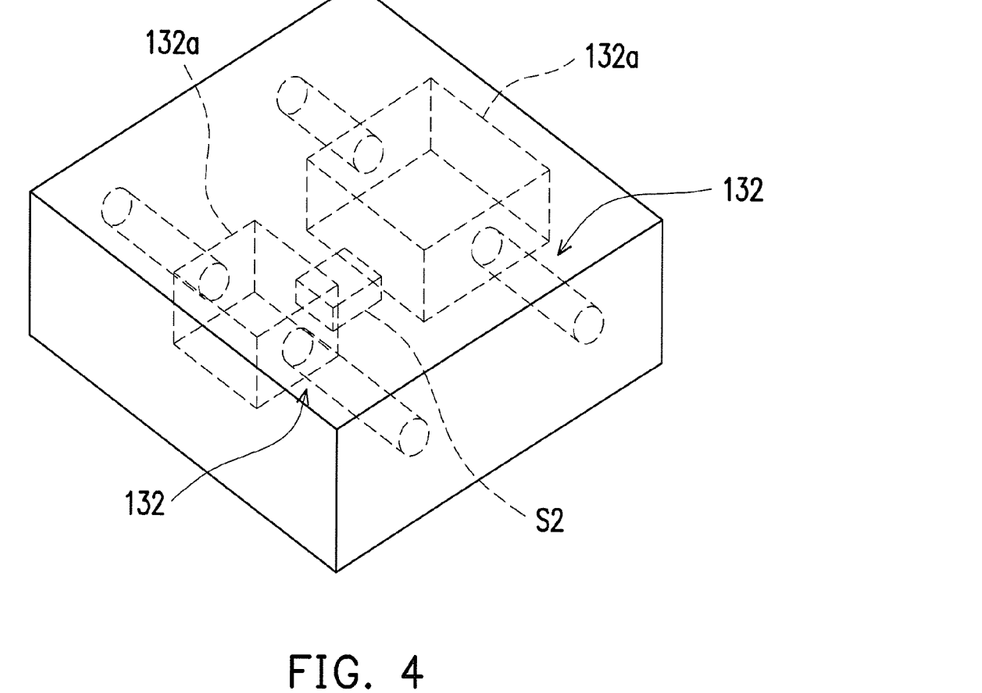
FIG. 4 is a view illustrating a specific structure of a flow-buffer unit according to an embodiment of the disclosure.
Figure 5:
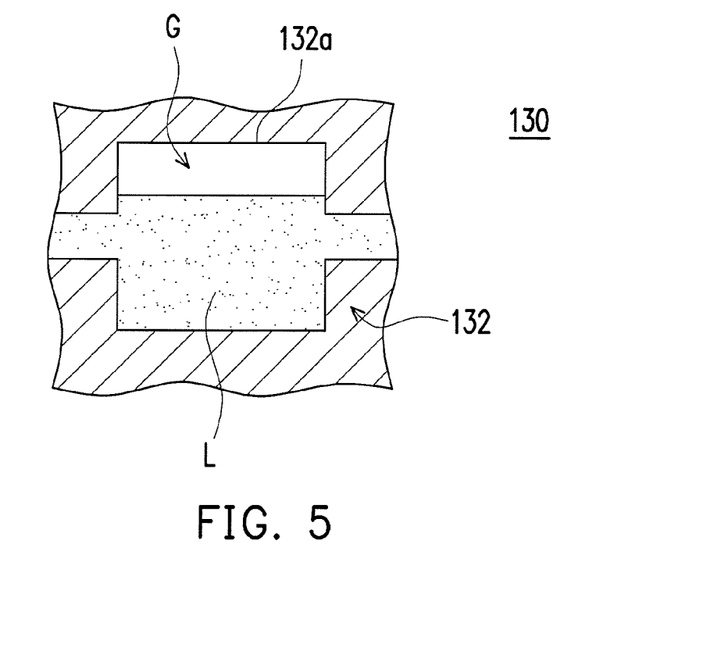
FIG. 5 is a partial cross-sectional view illustrating the flow-buffer unit shown in FIG. 4.

In the following, the flow-buffer unit according to an embodiment of the disclosure is described in detail in the following. FIG. 4 is a view illustrating an embodiment of the flow-buffer unit shown in FIG. 1. FIG. 5 is a partial cross-sectional view illustrating the flow-buffer unit shown in FIG. 4. Referring to FIGS. 4 and 5, in the flow-buffer unit 130 of this embodiment, each of the channels 132 includes a chamber 132a, and the chambers 132a are respectively configured to accommodate the first fluid and the second fluid. As shown in FIG. 5, by controlling a flow rate of the fluid, the chamber 132a in each of the channels 132 has a space to accommodate a gas G. In addition, the flow-buffer unit 130 may make use of a pressure of the gas G to perform buffering on a fluid L (i.e., the first fluid or the second fluid) in the chamber 132a. In other embodiments, the flow-buffer unit 130 may perform buffering in other ways, and the disclosure does not intend to impose a limitation in this regard.

Figure 6:
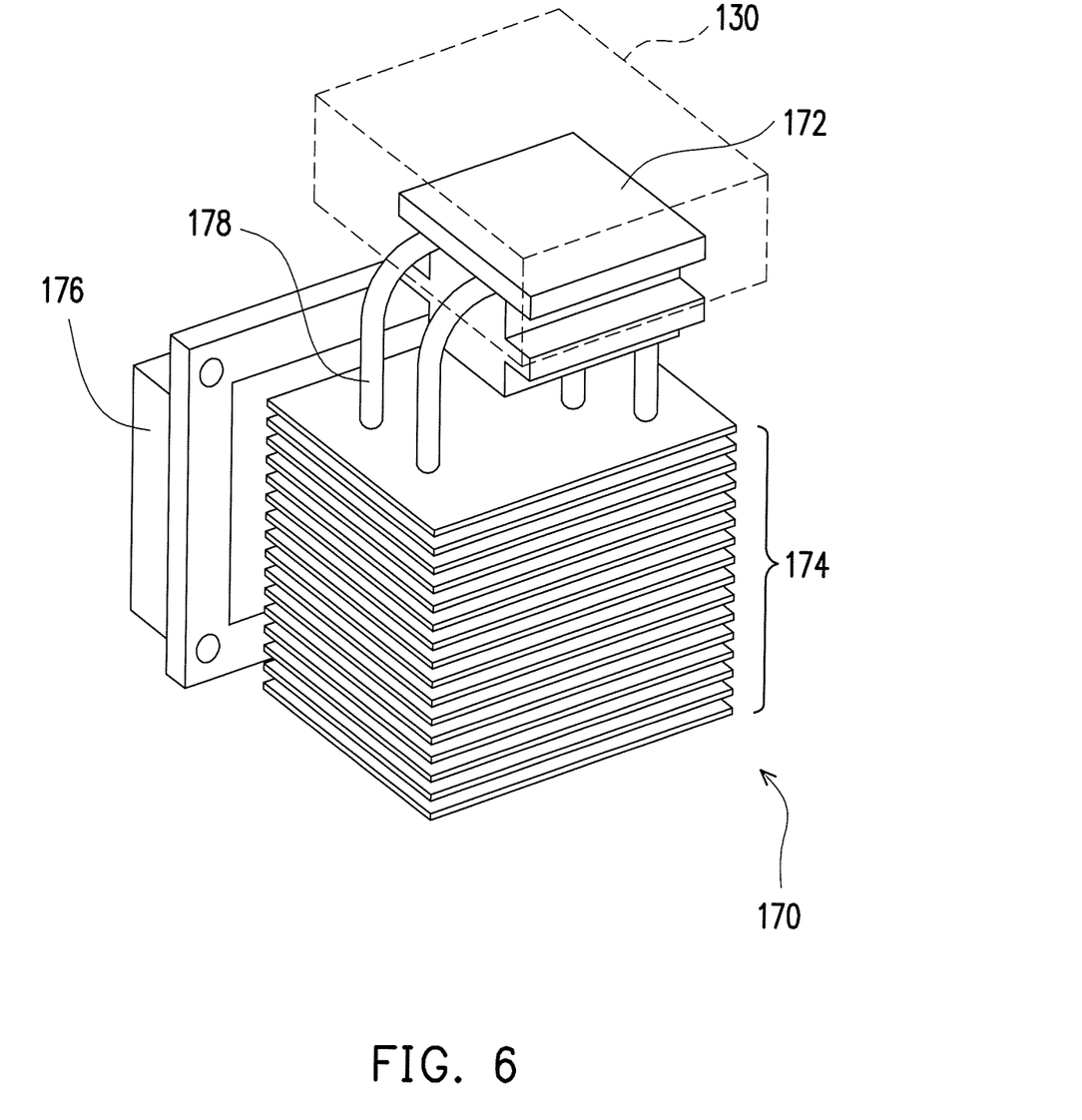
FIG. 6 is a view illustrating a specific structure of a temperature control unit according to an embodiment of the disclosure.

In the following, the temperature control unit of this embodiment is described in detail with reference to the drawings. FIG. 6 is a view illustrating an embodiment the temperature control unit shown in FIG. 1. Referring to FIG. 6, the temperature control unit 170 of this embodiment includes a cooling chip 172, a heat dissipating fin set 174, and a heat dissipating fan 176. The cooling chip 172 is connected to the flow-buffer unit 130 to control the temperatures of the first fluid and the second fluid in the flow-buffer unit 130. The heat dissipating fin set 170 is connected to the cooling chip 172 through a heat pipe 178 to receive and dissipate heat from the cooling chip 172. The heat dissipating fan 176 is disposed at a side of the heat dissipating fin set 174 to generate a heat dissipating air flow and dissipate the heat of the heat dissipating fin set 174. In other embodiments, the temperature control unit 170 may be a temperature control apparatus in other suitable forms, and the disclosure is not limited to the above.

Figure 7:
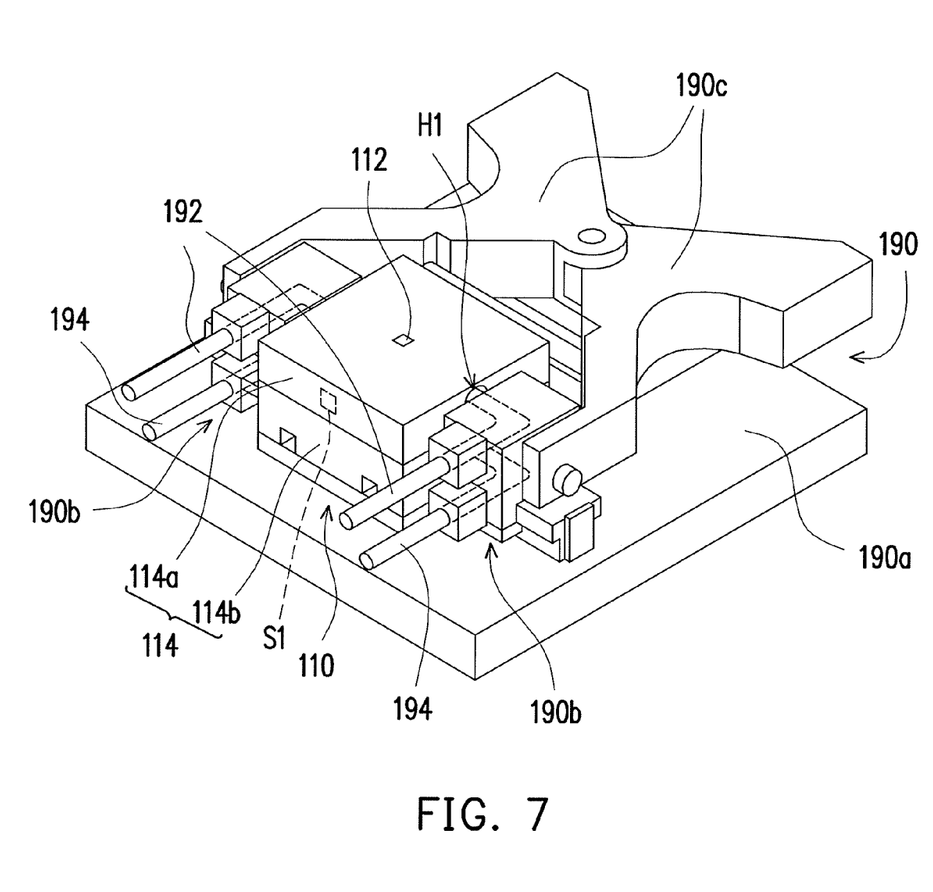
FIG. 7 is a view illustrating an embodiment where the carrier shown in FIG. 1 is clipped by a clamp.

The electron microscope 100 may further include a clamp to clip the carrier 110 and make the disposal of the carrier 110 easier. Details in this respect are described in the following with reference to the drawings. FIG. 7 is a view illustrating that the carrier shown in FIG. 1 is clipped by the clamp. Referring to FIG. 7, the electron microscope 100 includes a clamp 190. The clamp 190 is suitable to clip the body 114 of the carrier 110 and has a first flow guiding structure 192, such as a tube member, etc. When the clamp 190 clips the body 114 of the carrier 110, the first flow guiding structure 192 is connected to the first passage 114c (shown in FIG. 2) inside the carrier 110, and the first flow path P1 (shown in FIGS. 1 and 2) passes through the first flow guiding structure 192, so as to guide the first fluid to flow through the carrier 110 by using the first flow guiding structure 192. In addition, the first flow guiding structure 192 connected to the carrier 110 is configured to seal an opening H1 of the first passage 114c.

In an embodiment shown in FIG. 7, the clamp 190 may further include a second flow guiding structure 194. An arrangement relation between the second flow guiding structure 194 and the second passage 114d shown in FIG. 2 is the same as an arrangement relation between the first flow guiding structure 192 and the first passage 114c shown in FIG. 2. Details in this respect are described in the following. When the clamp 190 clips the body 114 of the carrier 110, the second flow guiding structure 194 is connected to the second passage 114c (shown in FIG. 2) inside the carrier 110, and the second flow path P2 (shown in FIGS. 1 and 2) passes through the second flow guiding structure 194, so as to guide the second fluid to flow through the carrier 110 by using the second flow guiding structure 194. In addition, the second flow guiding structure 194 connected to the carrier 110 is configured to seal an opening H2 (shown in FIG. 2) of the second passage 114d.

The clamp 190 in this embodiment includes a base 190a, two clipping members 190b, and two handles 190c. The base 190a is adapted to carry the carrier 110. The clipping members 190b are movably disposed on the base 190a. The handles 190 are pivoted with respect to each other and are respectively movably connected to the clipping members 190b. The handles 190c are adapted to be pivotally rotated with respect to each other by a force applied by the user, so as to drive the clipping members 190 to clip or release the carrier 110.

Figure 8:
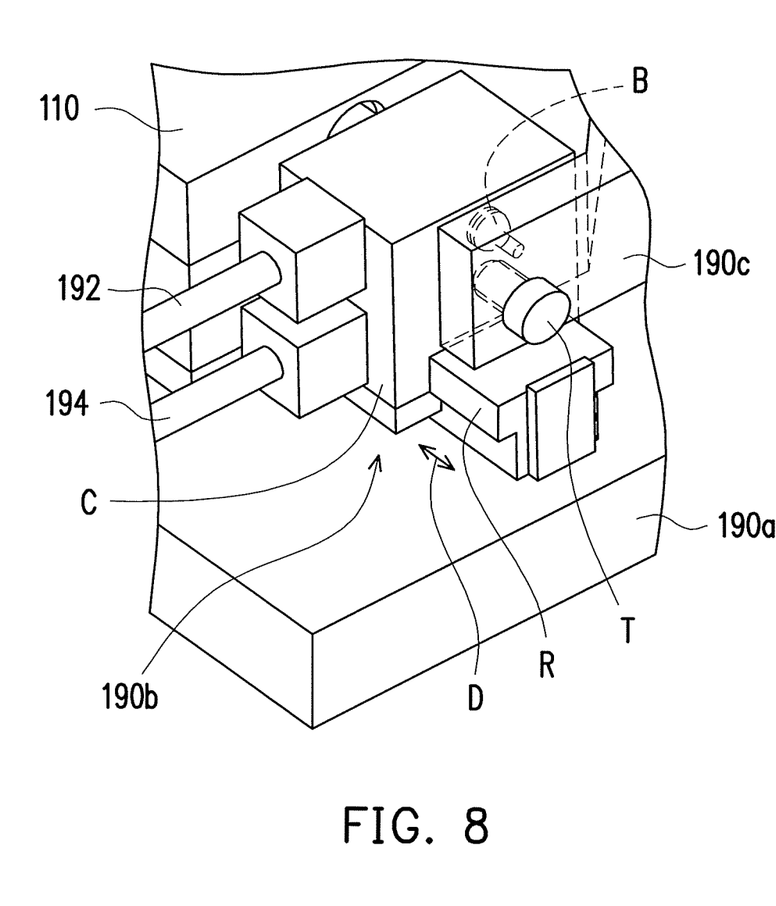
FIG. 8 is a partial enlarged view illustrating the clamp and the carrier shown in FIG. 7.

FIG. 8 is a partial enlarged view illustrating the clamp and the carrier shown in FIG. 7. Referring to FIG. 8, each of the clipping members 190 includes a clipping part C, a ball joint part B, a traction part T, and a guide rail part R. The guide rail part R is slidably disposed on the base 190a along a direction D, the clipping part C is disposed on the guide rail part R, the first flow guiding structure 192 and the second flow guiding structure 194 are disposed at the clip part C, the handle 190c is ball joined to the clipping part C through the ball joint part B, and the traction part T is connected between the handle 190c and the clipping part C. When the user applies a force to the handle 190c, the handle 190c drives the clipping part C through the traction part T to follow the guide rail part R and move in the direction D, so as to allow the clipping part C to clip or release the carrier 110. In other embodiments, the clamp may be designed as other suitable foul's. The disclosure does not intend to impose a limitation in this regard.

As shown in FIG. 7, a first temperature sensing element S1 is provided in the carrier 110 in an embodiment. The first temperature sensing element S1 is configured to sense temperature values of the first fluid and the second fluid flowing through the carrier 110. Also, as shown in FIG. 4, a second temperature sensing element S2 is provided in the flow-buffer unit 130 in an embodiment. The second temperature sensing element S2 is configured to sense temperature values of the first fluid and the second fluid flowing through the flow-buffer unit 130. Accordingly, the temperature control unit 170 shown in FIG. 1 is able to control the temperatures of the first fluid and the second fluid according to the temperature values sensed by the first temperature sensing element S1 and the second temperature sensing element S2. The first temperature sensing element S1 and the second temperature sensing element S2 are electrically connected to the control unit 100a shown in FIG. 1, for example, and operated under the control of the control unit 110a.

In the embodiment shown in FIG. 1, the first driving unit 120 driving the first fluid to flow is a pump. However, the disclosure is not limited thereto. In some other embodiments, the first driving unit may be an evacuating apparatus for a vacuum chamber. In addition to evacuating the first chamber by using the evacuating apparatus, the electron microscope further uses a pressure difference generated by using the evacuating apparatus to drive the first fluid to flow toward the carrier and through the sample by utilizing the siphon principle. Details in this respect are described in the following.

Figure 9:
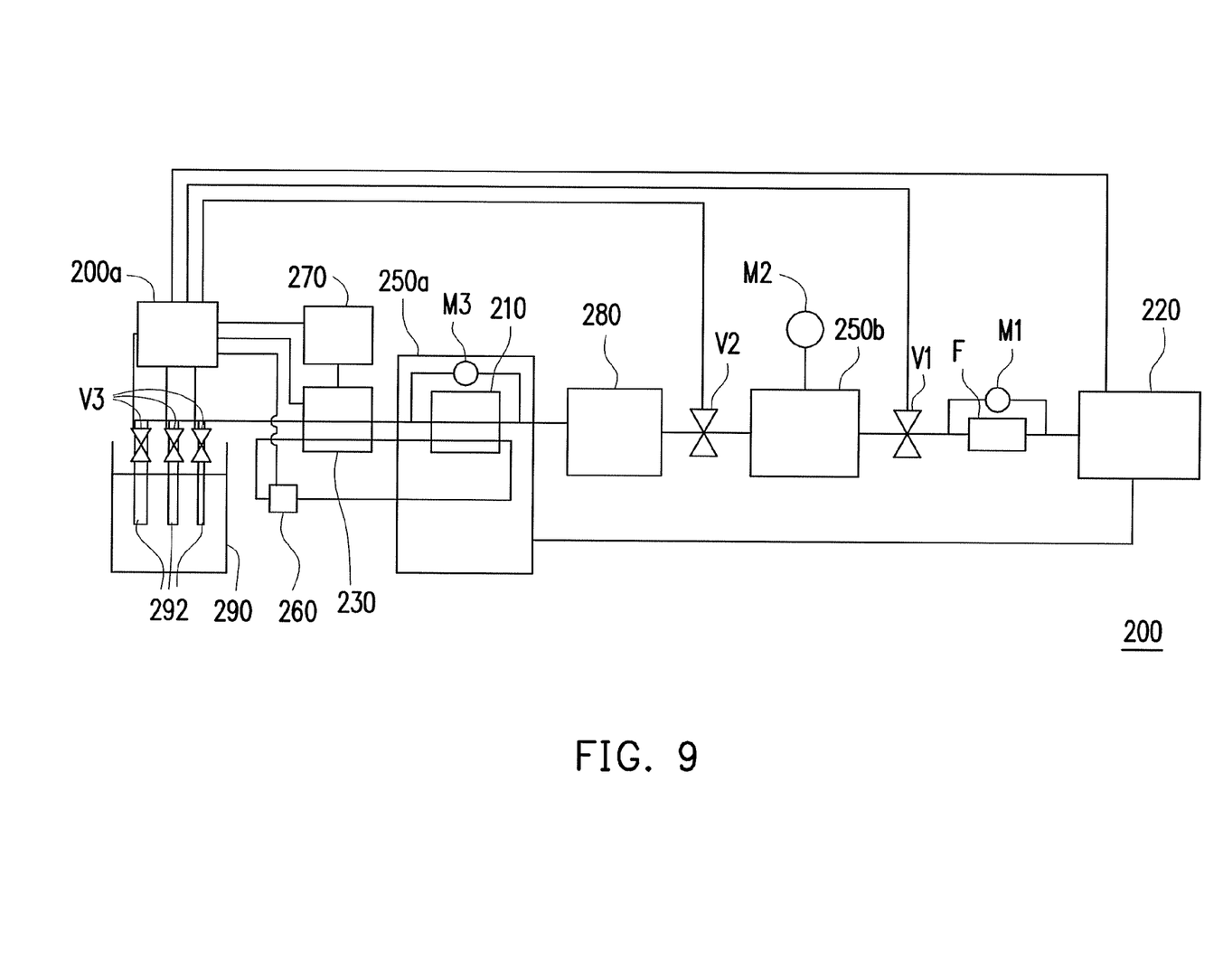
FIG. 9 is a schematic view illustrating some components of an electron microscope according to another embodiment of the disclosure.

FIG. 9 is a schematic view illustrating some components of an electron microscope according to another embodiment of the disclosure. In an electron microscope 200 shown in FIG. 9, the arrangement and operations of a control unit 200a, a carrier 210, a flow-buffer unit 230, a first chamber 250a, a second driving unit 260, a temperature control unit 270 are similar to those of the control unit 100a, the carrier 110, the flow-buffer unit 130, the first chamber 150a, the second driving unit 160, and the temperature control unit 170 shown in FIGS. 1 to 6. Thus, details in this respect will not be repeated in the following. The electron microscope 200 may further include an accommodating unit 290 to accommodate the first fluid and be connected to the carrier 210.

The embodiments of the electron microscope 200 and the electron microscope 100 differ in that a first driving unit 220 of the electron microscope 200 is not a pump, but an already existing evacuating apparatus of the electron microscope 200, and the electron microscope 200 further includes a second chamber 250b. The evacuating apparatus (i.e., the first driving unit 220) is connected to the first chamber 250a and evacuates the first chamber 250a for observing the sample inside the carrier 210. The second chamber 250b is connected between the evacuating apparatus (i.e., the first driving unit 220) and the accommodating unit 290, and the carrier 210 is disposed between the second chamber 250b and the accommodating unit 290. A valve V1 (e.g., an electromagnetic valve) is disposed between the evacuating apparatus (i.e., the first driving unit 220) and the second chamber 250b, and a valve V2 (e.g., an electromagnetic valve) is disposed between the second chamber 250b and the first chamber 250a. When the valve V1 is open and the valve V2 is closed, the evacuating apparatus (i.e., the first driving unit 220) may evacuate the second chamber 250b.

Also, when the valve V2 is open and the valve V1 is closed, a pressure difference between the vacuum second chamber 250b and the accommodating unit 290 may drive the first fluid to flow from the accommodating unit 290 toward the carrier 210, so that the first fluid may flow from the accommodating unit 290 toward the carrier 210 by utilizing the siphon principle. Thus, the first driving unit 220 is simultaneously capable of driving the first fluid to flow and evacuating the first chamber 250a. Thus, it does not require an additional pump as the driving source of the first fluid, and the electron microscope 200 may thus be simplified. Driving the fluid to flow through evacuation makes a fluid pressure lower, thereby reducing a chance that the film is damaged due to flowing of the fluid. In other embodiments, the electron microscope 200 may use an already existing evacuating apparatus to evacuate the first chamber 250a, and use another evacuating apparatus to drive the first fluid to flow. The disclosure does not intend to impose a limitation in this regard.

As shown in FIG. 9, a filter F is provided between the first driving unit 220 and the valve V1. The filter F is configured to filter a gas that flows from the valve V1 toward the first driving unit 220. A collecting unit 280 is provided between the valve V2 and the carrier 210. The collecting unit 280 is configured to collect a metabolite of the sample in the carrier 210. Also, a differential gauge M1 is provided at the filter F, a pressure gauge M2 is provided at the second chamber 250b, and a differential gauge M3 is provided at the carrier 210. The differential gauge M1, the pressure gauge G2, and the differential gauge M3 are respectively configured to measure pressure values at the filter F, the second chamber 250b, and the carrier 210, such that the first driving unit 220, the valve V1, and the valve V2 are able to be operated accordingly to smoothly drive the first fluid to flow.

Referring to FIG. 9, the accommodating unit 290 may have a plurality of conduits 292. The conduits 292 are connected to the carrier 210 and respectively have different diameters. The first fluid may flow out of the accommodating unit 290 through any one of the conduits 292. In addition, the greater the diameter of the conduit 292, the higher a flow rate that the first fluid flows out of the accommodating unit 290 through the conduit 292 by utilizing the principle of siphon becomes. Accordingly, the conduit 292 with a suitable diameter may be chosen to transport the first fluid based on the flow rate. Each of the conduits 292 has a valve V3. Each valve V3 is configured to control whether the first fluid flows out through the corresponding conduit 292.

In view of the foregoing, in the electron microscope according to the embodiments of the disclosure, buffering is performed on the first fluid by the flow-buffer unit and then the first fluid flows into the carrier. In addition, the flow-buffer inclined surface may also be used to perform buffering on the first fluid again, so as to further reduce a disturbance of the first fluid flowing through the sample in the carrier. Thus, the user is able to observe the sample by using the electron microscope. Moreover, in addition to the first passage provided for the first fluid to flow through, the second passage stacked with respect to the first fluid is also provided in the carrier for the second fluid to flow through, so that the temperature of the first fluid may be adjusted by using the second fluid. In this way, the sample may be observed at an expected suitable temperature. Furthermore, the flow-buffer unit may be further used to perform buffering on the first fluid and the second fluid at the same time, and the temperature control unit integrated into the flow-buffer unit may also be used to simultaneously control the temperatures of the first fluid and the second fluid, so as to improve the flow-buffer and temperature control efficiencies of the electron microscope. The already existing evacuation apparatus of the electron microscope may be further used to drive the first fluid to flow. In this way, it does not require an additional pump as the driving source of the first fluid, and the space and cost of the electron scope may thus be reduced.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An electron microscope having a carrier, comprising:
   the carrier, carrying a sample, comprising:
      a body, having a first passage and a second passage, wherein the first passage and the second passage are stacked with respect to each other; and
      a film, disposed at the body and carrying the sample, wherein the sample is located in the first passage, a first fluid flows along the first passage and passes through the sample, and a second fluid flows along the second passage to adjust a temperature of the first fluid;
   a first driving unit, driving the first fluid to flow along a first flow path, wherein the first flow path passes through the sample;
   a flow-buffer unit, disposed on the first flow path to perform buffering on the first fluid, wherein the first fluid flows through the flow-buffer unit and the carrier; and
   an electron source, providing an electron beam to the sample.

2. The electron microscope as claimed in claim 1,
wherein the first passage has a flow-buffer inclined surface,
and the first fluid flows along the first passage to pass through the flow-buffer inclined surface.

3. The electron microscope as claimed in claim 1, wherein the flow-buffer unit has two channels, the first fluid flows through one of the channels and the sample, the second fluid flows through another one of the channels and the carrier to adjust the temperature of the first fluid, and the flow-buffer unit respectively performs buffering on the first fluid and the second fluid.

4. The electron microscope as claimed in claim 1, comprising a first chamber, wherein the carrier is disposed inside the first chamber, the first driving unit is an evacuation module, and the evacuation module evacuates the first chamber and drives the first fluid to flow through the sample.

5. The electron microscope as claimed in claim 1, comprising a clamp, wherein the clamp is adapted to clip the carrier and has a first flow guiding structure, and when the clamp clips the carrier, the first flow guiding structure is connected to the carrier and the first flow path passes through the first flow guiding structure.

6. The electron microscope as claimed in claim 5, wherein the second fluid flows through the carrier along a second flow path to adjust the temperature of the first fluid, the clamp has a second flow guiding structure, and when the clamp clips the carrier, the second flow guiding structure is connected to the carrier and the second flow path passes through the second flow guiding structure.

7. The electron microscope as claimed in claim 5, wherein the clamp comprises:
a base, adapted to carry the carrier;
two clipping members, movably disposed on the base; and
two handles, pivoted with respect each other and respectively movably connected to the clipping members, wherein the handles are adapted to be pivotally rotated with respect to each other and drive the clipping members to clip or release the carrier.

8. The electron microscope as claimed in claim 1, wherein a first temperature sensing element is provided in the carrier.

9. The electron microscope as claimed in claim 1, wherein a second temperature sensing element is provided in the flow-buffer unit.

10. An electron microscope having a carrier, comprising:
the carrier, comprising:
a body, having a first passage and a second passage, wherein the first passage and the second passage are stacked with respect to each other; and
a film, disposed at the body and carrying the sample, wherein the sample is located in the first passage, a first fluid flows along the first passage and passes through the sample, and a second fluid flows along the second passage to adjust a temperature of the first fluid,
wherein the first passage has a flow-buffer inclined surface,
and the first fluid flows along the first passage to pass through the flow-buffer inclined surface; and
an electron source, providing an electron beam to the sample.

11. The electron microscope as claimed in claim 10, comprising a protrusion structure, wherein the protrusion structure is located in the first passage to constitute the flow-buffer inclined surface.

12. The electron microscope as claimed in claim 10, further comprising a flow-buffer unit, wherein the first fluid flows through the flow-buffer unit and the carrier, and the flow-buffer unit performs buffering on the first fluid.

13. An electron microscope having a carrier, comprising:
the carrier, comprising:
a body, having a first passage and a second passage, wherein the first passage and the second passage are stacked with respect to each other; and
a film, disposed at the body and carrying a sample, wherein the sample is located in the first passage, a first fluid flows along the first passage and passes through the sample, and a second fluid flows along the second passage to adjust a temperature of the first fluid; and
an electron source, providing an electron beam to the sample.

14. The electron microscope as claimed in claim 13, comprising a temperature control unit controlling a temperature of the second fluid.

15. An electron microscope having a carrier, comprising:
the carrier, having a film carrying a sample, comprising;
a body, having a first passage and a second passage, wherein the first passage and the second passage are stacked with respect to each other; and
a film, disposed at the body and carrying the sample, wherein the sample is located in the first passage, a first fluid flows along the first passage and passes through the sample, and a second fluid flows along the second passage to adjust a temperature of the first fluid;
a flow-buffer unit, having two channels, wherein the first fluid flows through one of the channels and the sample, the second fluid flows through another one of the channels and the carrier to adjust the temperature of the first fluid, and the flow-buffer unit respectively performs buffering on the first fluid and the second fluid; and
an electron source, providing an electron beam to the sample.

16. The electron microscope as claimed in claim 15, wherein the flow-buffer unit respectively applies pressures to the channels, so as to perform buffering on the first fluid and the second fluid.

17. The electron microscope as claimed in claim 16, wherein a gas is provided in each of the channels, and the flow-buffer unit performs buffering on the first fluid or the second fluid by using a pressure of the gas.

18. The electron microscope as claimed in claim 15, comprising a temperature control unit, wherein the temperature control unit is connected to the flow-buffer unit and controls temperatures of the first fluid and the second fluid flowing through the channels.

19. The electron microscope as claimed in claim 18, wherein the temperature control unit comprises:
a cooling chip, connected to the flow-buffer unit;
a heat dissipating fin set, connected to the cooling chip; and
a heat dissipating fan, disposed at a side of the heat dissipating fin set.

20. An electron microscope having a carrier, comprising:
a first chamber;
the carrier, disposed inside the first chamber and carrying a sample, comprising;
a body, having a first passage and a second passage, wherein the first passage and the second passage are stacked with respect to each other; and a film, disposed at the body and carrying the sample, wherein the sample is located in the first passage, a first fluid flows along the first passage and passes through the sample, and a second fluid flows along the second passage to adjust a temperature of the first fluid;

an evacuation apparatus, evacuating the first chamber and driving the first fluid to flow through the sample; and an electron source, providing an electron beam to the sample.

21. The electron microscope as claimed in claim 20, comprising an accommodating unit and a second chamber, wherein the evacuating apparatus is connected to the first chamber and evacuates the first chamber, the accommodating unit is configured to accommodate the first fluid and connected to the carrier, the second chamber is connected between the evacuating apparatus and the accommodating unit, the evacuating apparatus evacuates the second chamber, so as to drive the first fluid to flow from the accommodating unit toward the carrier by using a pressure difference between the second chamber and the accommodating unit.

22. The electron microscope as claimed in claim 20, comprising an accommodating unit, wherein the accommodating unit accommodates the first fluid and has a plurality of conduits, the conduits are connected to the carrier and respectively have different diameters, and the first fluid flows out of the accommodating unit from any one of the conduits.

* * * * *